United States Patent [19]
Adam et al.

[11] 4,152,423
[45] May 1, 1979

[54] IMMUNOLOGICAL AGENTS

[75] Inventors: Arlette Adam, Palaiseau, France; Frank M. Berger, Princeton, N.J.; Louis Chedid, Paris, France; Edgar Lederer, Sceaux, France; Jean-Francois Petit, Paris, France

[73] Assignee: Agence Nationale de Valorisation de la Recherche (ANVAR), Neuilly-sur-Seine, France

[21] Appl. No.: 806,987

[22] Filed: Jun. 16, 1977

Related U.S. Application Data

[62] Division of Ser. No. 307,614, Nov. 17, 1972, Pat. No. 4,036,953.

[30] Foreign Application Priority Data

Nov. 19, 1971 [FR] France ................................ 71.41610

[51] Int. Cl.[2] ...................... A61K 39/02; A61K 39/04
[52] U.S. Cl. .................................................... 424/92
[58] Field of Search ........................................ 424/92

[56] References Cited
PUBLICATIONS

Engibarov–Chem. Abst., vol. 68, (1968), p. 85115t.

*Primary Examiner*—Sam Rosen
*Attorney, Agent, or Firm*—Weiser, Stapler & Spivak

[57] ABSTRACT

The present invention relates to novel immunological agents effective as adjuvants for stimulating an immune response to various types of antigens. The adjuvants do not cause objectionable reactions and they are easily purified. The invention additionally relates to a process for producing the novel adjuvants.

22 Claims, No Drawings

IMMUNOLOGICAL AGENTS

This is a division, of application Ser. No. 307,614, filed Nov. 17, 1972, now U.S. Pat. No. 4,036,953.

The present invention relates to agents effective as immunological adjuvants for stimulating, in a host, the immune response to various kinds of antigens. The invention relates more particularly to adjuvants capable of enhancing and promoting the activity of weak immunogens.

Specifically, this invention relates to adjuvant materials usable for the immunization of warm-blooded animals against bacterial, viral and parasitic infections, as well as against various tissue antigens, both of normal and of pathological origin and, specifically, against tumors.

Materials having adjuvant properties have been known for some time. For instance, it is well known that materials such as mycobacterial cells and mycobacterial cell walls enhance the production of antibodies in the host and, in particular, increase the host resistance to infections caused by numerous microorganisms. The known materials of this kind, such as Freund's complete adjuvant which contains whole mycobacterial cells, have been found undesirable for therapeutical usage owing to highly objectionable reactions caused thereby. Thus, they may enhance the host's sensitivity to endotoxin, cause a hypersensitivity to tuberculin and induce lung granuloma, lymphoid hyperplasia and, under certain circumstances, an experimental polyarthritis in the rat. Further, prior to the present invention, adjuvants based on mycobacterial substances, have been difficult to purify owing to their insolubility.

Water-soluble agents, extracted from mycobacteria, Nocardia cells and related microorganisms, which form the subject-matter of this invention, are free of the drawbacks inherent to previously known mycobacterial materials.

Such novel agents are free of the noxious effects inherent to the previously known preparations. These novel agents possess an adjuvant activity which is generally more potent than that of mycobacterial preparations including mycobacterial whole cells, without the objectionable effects inherent to previously known products. Furthermore, this new agent can, under suitable conditions, provide the adjuvant action upon being suspended together with antigen in an aqueous solution, if desired in the presence of substances such as aluminum hydroxide or calcium phosphate. Finally, the water-solubility of these agents makes their purification easier to perform.

The preferred agents included among those within the scope of the invention, endowed with all the advantageous properties of mycobacterial whole cells without having the objectionable secondary effects thereof, are contained in the aqueous medium in which delipidated cell walls of mycobacteria, Nocardia cells or related microorganisms have been digested in the presence of a murolytic enzyme, such as lysozyme.

Agents according to the invention are producted from cells of mycobacteria, both pathogenic and nonpathogenic, Nocardia cells and related microorganisms. As examples of mycobacteria usable as starting material in the production of adjuvants, according to the invention, there may be mentioned, inter alia, *Mycobacterium tubercolosis*, var hominis or bovis and, in particular, the Bacille Calmette Guerin (BCG); *Mycobacterium kansasil; Mycobacterium smegmatis*, or other organisms belonging to genus Mycobacterium.

The agents according to the invention can be produced by a process essentially comprising: cultivating a strain of mycobacteria, Nocardia cells or related microorganisms; recovering the cells of the cultivated strain; causing disruption thereof; taking up the disrupted cell walls, such as by differential centrifuging; separating and removing waxes, free lipids, proteins and nucleic acids; causing the delipidated material from the cell walls to be digested by means of a murolytic enzyme, such as lysozyme; eliminating the solid residue; and collecting the aqueous fraction containing said soluble agents.

In accordance with preferred embodiments of the process of the invention, the objectionable proteins are removed by means of a treatment of the material from disrupted cell walls with proteolytic enzymes, such as trypsin and chymotrypsin, whereas nucleic acids are removed by treating said material with desoxyribonuclease or DNAse, and finally free lipids and waxes are eliminated with neutral solvents such as acetone, alcohol, chloroform or mixtures of such solvents.

The agents according to the invention can be obtained in a purified form by subjecting the aqueous medium to filtration through a column of gel of polydextran or a similar material such as the gel sold under the trademark "SEPHADEX G75" or "SEPHADEX G50".

The agents of the invention seem to be formed by oligomers or portions thereof, the monomer units of said oligomers having a chemical structure similar to that of monomer units of the cell walls of microorganisms from which they have been extracted, except that the lipid moiety may be absent, or in any case, of a very small size. The monomer units of the walls include a mucopeptide combined with a glycolipid containing an arabinogalactan. A hypothetical structure of a monomer from mycobacterial cell walls (molecular weight: about 3000) has been set forth by E. Lederer in an article dealing with the chemistry of mycobacterial cell walls and published in "Pure and Applied Chemistry, 25, 1971, 135".

The agents according to the invention contain the usual aminosugars and amino-acids of the cell walls.

In the following there is set forth a typical chemical analysis of a preferred agent forming the subject matter of the invention, obtained from mycobacteria of the species *Mycobacterium smegmatis*:

C=42.84%; H=6.49%; N=3.96%; P=0.1%; S=0.

Aminosugars, consisting essentially of D-glucosamine and D-muramic acid, in equimolar proportions . . . 12–15%

Amino-acids consisting essentially of L- and D-alanine, D-glutamic acid and meso-$\chi$-$\epsilon$-diamino-pimelic acid, in a ratio of 1.3:1:1 . . . 12–15%

Neutral sugars consisting essentially of D-arabinose and D-galactose, in an approximate ratio of 2:1 . . . 60–70%

Lipids . . . less than 5%

$[2]_D$ in water: +11.3°±0.5°

Their sedimentation coefficient in a phosphate buffer, pH 7.0$\mu$=0.1, at 20° C. and at a concentration of C=4.8 mg/ml, is of the order of . . . $20=2,05

U.V. spectrum is characterized by a terminal absorption less than 230 nm.

I.R. spectrum shows bands at 1650 and 1520 cm$^{-1}$ (amides) and at 1000–1100 cm$^{-1}$ (—OH groups).

Moreover, agents included within the scope of the invention remain stable at room temperature during at least several months and may be lyophilised without loss of activity. After lyophilisation, said agents form a flaky material, which is snow-white, readily soluble in water and providing a slightly opalescent solution. Said agents are not soluble in ether, chloroform, acetone and mixtures of ethanol-chloroform; in an ultracentrifuge, the solutions of the agent behave like a homogeneous slightly polydisperse, macromolecular system.

Further features of the invention will become clear upon reading the following description concerning preferred embodiments of cultivation and extraction of materials according to the invention, said description being given merely by way of an example without limiting the scope of the invention, as defined by the appended claims.

EXAMPLE 1

*Mycobacterium smegmatis* cells, a strain of which has been deposited at "American Type Culture Collection" under N° ATCC NBR 21732, are cultivated in Roux bottles on Sauton medium during about 12 days at 37° C. They are harvested by filtration on filter paper, washed with distilled water and stored at −20° C. until use.

A hundred grams of cells are suspended in 500 ml of distilled water by cold-mixing in a Waring blender, which has been precooled, until the supension becomes homogenous. These cells are then disrupted in a precooled French press, operated in a cold room under a pressure of 420 kg/sq.cm. After a first pass, there is added 1 mg DNAse to reduce viscosity, whereafter the suspension is passed a second time through French press. In addition to the disintegration of cells by mechanical pressure, the cells may also be disrupted by sonic vibration of 30 ml of suspension during 25 minutes (5×5 minutes) in a sonic oscillator, previously cooled and operated at 10 kc/sec., as well as by disrupting the cells by means of freezing-thawing, by treating them with a zeolite shaking them together with glass balls or by any conventional means usable for the disruption of microbial cells.

The resulting suspension is centrifuged three times during 15 minutes at 800 g in a refrigerated centrifuge. The pellets consisting of non-disrupted cells, are discarded. The ultimate supernatant liquor is centrifuged during an hour at 27,500 g; the pellets of cell-wall materials are returned into a suspension of 750 ml of sodium phosphate buffer (0.066 M, pH 7.8) having added thereto 125 mg trypsin, 125 mg chymotrypsin and a small portion of an antiseptic agent such as toluene, in order to preclude any bacterial contamination. The product is kept in an incubator overnight at ordinary room temperature with magnetic stirring and, thereafter, the mixture is centrifuged during an hour at 27,500 g. The pellets of cell-wall materials are washed by putting them back into suspension and centrifuging, three times with cold phosphate buffer and three times with cold distilled water.

Cell-wall material is thereafter delipidated at normal room temperature with neutral solvents. To this end, said material is put into suspension in about 30 volumes of solvent which is allowed to act during about one day with stirring. Cell-wall material is thus delipidated, three times with acetone, three times with ethanol-ether (1/1), three times with chloroform and three times with chloroform-methanol (2:1); the material is then dried with acetone. Delipidated and dried cell-wall material can be stored at room temperature until usage.

One gram of delipidated cell-wall material, obtained as aforesaid, is suspended in 250 ml of a 0.1 M solution of ammonium acetate, pH 6.2; the suspension is kept overnight in the cold with a few drops of toluene. The material is filtered on a sintered-glass filter, washed with ethanol and chloroform. The washed material is put back in suspension in 150 ml of ammonium acetate (0.1 M, pH 6.2) having added thereto 12 mg lysozyme and a few drops of toluene; the product is kept overnight in an incubator at 37° C. with stirring. After filtering on sintered glass, the residue is treated once more with lysozyme in the same conditions as before. Both filtrates are mixed, lyophilised, redissolved in water and lyophilised until removal of ammonium acetate. Yield: about 90 mg of crude water-soluble product per gram of dried delipidated cell-wall material.

The water-soluble crude product (500 mg) is filtered through a column of "SEPHADEX G50" (height: 80 cm, diameter 2.5 cm) in equilibrium with 0.1 N acetic acid. The first peak egressing from the column, well separated from the remaining products, contains the agent under consideration in a purified state (150 mg), said agent being characterized by the analytical data given above.

Filtering on a column of "SEPHADEX G75" yields a broader peak including a shoulder. Said peak appears to include two fractions of the same composition, but differing in all likelihood by their molecular weights only.

Fractions corresponding to the second peak of "SEPHADEX G50" column, which is clearly distinct from the first, contain substances of lower molecular weight, which are also included within the scope of the invention, said substances having pharmacological activities disclosed thereafter and being usable for purposes which will also appear in the following.

EXAMPLE 2

A similar preparation has been obtained from *Mycobacterium tuberculosis* var bovis, BGG strain (institut Pasteur).

Bacilli have been cultivated 15 days on Sauton medium 37° C., washed with distilled water and kept at −20° C. until use.

Cell-walls were obtained by treatment in a French press and differential centrifugation, thereafter treated with trypsin and chymotrypsin, and delipidated exactly under the same conditions as in Example 1 for *M. smegmatis*. They were then put back into suspension in ammonium acetate and digested by lysozyme exactly like in Example 1.

The obtained filtrate was lyophilised and redissolved in water several times to eliminate ammonium acetate: the thus obtained product is an adjuvant as efficient as the product obtained from *M. smegmatis*.

EXAMPLE 3

A similar formulation has been obtained from *Mycobacterium kansasii*, strain P 21 Runyon.

Bacilli were cultivated during 28 days on Sauton medium at 37° C., were killed by phenol (2%) during 48 hours, thereafter washed with distilled water and kept at −20° C. until use. Thereafter they were delipidated in succession by alcohol-ether (1:1), chloroform, chloroform-methanol (2:1), dried with acetate; the delipidation with each of these solvents was repeated three times, using on each occasion a volume of solvent equal to 30 times the initial weight of bacilli.

These cells were suspended at a rate of 1 g of dried bacilli per 25 ml distilled water and subjected to ultrasonic energy, by fractions of 30 ml during 25 minutes in an apparatus of 250 watts, 10 kg/sec. The non-disrupted bacilli were removed by centrifuging (10 minutes, 500 g), put back into suspension and subjected to centrifugation (3 times). Walls were obtained by centrifuging (50 minutes, 27500 g). They were digested by trypsin and chymotrypsin, thereafter washed in the same way as in Example 1 and 2.

They were digested by lysozymes in the same conditions as in the preceding examples. The filtrate was freed by lyophilisation from ammonium acetate. The product possessed likewise adjuvant properties.

Pharmalogical properties of the agents according to the invention

The agents of the invention, prepared as aforesaid, possess a powerful activity as adjuvants and are free of the serious drawbacks which were responsible for the limitations of therapeutic usage by mycobacteria and Freund's adjuvant. These highly advantageous features are evidenced by the pharmacological tests described hereunder.

In the following, the term "Substance A" refers to the agent contained in the elution fractions on "SEPHADEX" gel corresponding to the aforesaid "first peak".

The expression "Substance B" is applied to identify products resulting from lyophilisation of fractions which correspond to the "second peak" of elution in Example 1 (on "SEPHADEX G50").

A. Demonstration of the adjuvant activity of "Substances A"

When, in the tests described thereunder, "Substance A" has been suspended in a mineral oil, the oil was a product sold under the trademark "Bayol F", in the presence of a dispersing agent such as glycerol monooleate or the dispersing agent available under the trademark "Arlacel A". In numerous cases, properties of "Substance A" have been compared with those of whole mycobacteria or mycobacterial fractions, those of conventional Freund's complete adjuvant (FCA), those of the Freund's incomplete adjuvant (FIA), i.e. the adjuvant containing no bacteria.

In each case, "Substance A" was obtained from *Mycobacterium smegmatis*, except if a different source has been expressly stipulated. Further, the term "Crude Substance A" represents the water-soluble product obtained by digestion with lysozyme but without purification on "SEPHADEX" gel.

1. Adjuvant activity of "Substance A", on the rate of serum antibodies with respect to ovalbumin in guinea pigs; quantitative precipitation and passive hemo-agglutination.

A soluble antigen, namely ovalbumin, was added to "Substance A", to wax D (extracted from *M. tuberculosis*), to 6,6'-trehalose dimycolate known as "cord factor" and called by this name in the following (extracted from *M. kansasii*) and to Mycoside C (extracted from *M. butyricum*).

The mixture obtained in each case was added to incomplete Freund's adjuvant (FIA), then injected as an emulsion of the water-in-oil type into the foot-pad of guinea pigs. The controls comprised ovalbumin with incomplete Freund's adjuvant or complete Freund's adjuvant (FCA), the latter consisting of FIA and *M. butyricum cells*. The rates of antibodies with respect to ovalbumin were determined 21 days after injection. The induced antibody production was determined by quantitative precipitation in accordance with the method described by Gierer and Schramm (Zeit. fur Naturforsch., 1956, 116: 138), and by passive hemo-agglutination of erythrocytes coated with ovalbumin in the manner described by Stavitsky (J. Immunol., 1954, 72: 360–368). The results are summarized in Table I thereunder.

In this Table, there is shown the antibody rates after administration of the carrier alone and after administration of "Substance A" in an absolutely identical carrier. The Table shows that, as a rule, "Substance A" stimulated to a greater degree the production of antibodies than did the complete Freund's adjuvant. It is also shown, for comparison, that the said product was more active than wax D. The results indicate further the absence of adjuvant properties of both mycobacterial components previously isolated such as "cord factor" and mycoside C.

The numerical values appearing in the Table I correspond to the mean value of groups of 6 guinea pigs. The results are expressed in micrograms of antigen-antibody complex per ml of serum in the case of a quantitative precipitation and as a reciprocal of serum titration in the case of hemo-agglutination.

Table I

Adjuvant activity of "Substance A" and other mycobacterial fractions on the rate of serum antibodies with respect to ovalbumin in guinea pigs. Quantitative precipitation and passive hemo-agglutination.

| Product injected and dosages per guinea-pig | Quantitative precipitation | Hemo-agglutination (reciprocal of serum titration) |
|---|---|---|
| FCA | 3532 | 4200 |
| Controls FIA | 747 | 1770 |
| FIA + "Substance A" 1µg | 2016 | 2240 |
| FIA + "Substance A" 10µg | 4715 | 2660 |
| FIA + "Substance A" 50µg | 6867 | 5440 |
| FIA + wax D of *M.tuberculosis* 200µg | 1573 | 3730 |
| FIA + "cord factor" of *M.kansasii* 50µg | 584 | 400 |
| FIA + mycoside C of *M.butyricum* 50µg | 716 | 400 |

Finally, it has been demonstrated by immunoelectrophoresis that an antigen in the presence of "Substance A" as well as in the presence of a complete Freund's adjuvant produces certain immuno-globulins called γ2.

2. Comparative adjuvant properties of "Substance A" FIA and FCA estimated by Jerne's technique on mice, sheep erythrocytes being used as antigens.

"Substance A" also increases the immunitary response to particular antigens, such as sheep erythrocytes. "Substance A" was administered to mice with FIA intraperitoneously, together with $2 \times 10^7$ sheep erythrocytes in accordance with a method described by N. K. Jerne, A. A. Nordin and C. Harry in "Cell-bound Antibodies", Ed. B. Ames and H. Koprovski, Wistar Institute Press, Philadelphia, (1963).

The animals used as controls comprised a first group of mice having received an injection of sheep erythrocytes exclusively in a saline solute, a second group having received injections of sheep erythrocytes exclusively in incomplete Freund's adjuvant, and a third group having received injections of sheep erythrocytes in complete Freund's adjuvant.

Three days later, the number of antibody-forming cells is determined in the spleen; Table II A shows an increase of the number of antibody-forming cells in the spleen when sheep erythrocytes are injected together with FCA or with FIA with "Substance A".

Table 11A

|  | Number of plate-forming cells | Increase % |
|---|---|---|
| Controls { Sheep erythrocytes + saline | 646 | — |
| Sheep erythrocytes + FIA | 703 | 9 |
| Sheep erythrocytes + FCA | 1554 | 141 |
| Sheep erythrocytes, + FIA + 0.1 mg/kg | 1092 | 69 |
| Sheep erythrocytes + FIA + 1 mg/kg | 1800 | 179 |

In the following experiment adjuvant activity can be demonstrated in the absence of mineral oil and of a dispersing agent. The controls were injected with sheep red blood cells suspended only in saline or in FIA. Two other groups were treated with Substance A either in saline or suspended in FIA and the third group was treated with Substance B suspended in saline. All animals were sacrificed four days later and the number of plaque forming cells was evaluated. As can be seen in Table II B both Substances A and B exerted a strong adjuvant effect even when they were mixed with sheep red blood cells in saline.

Table 11 B

|  | Number of plate-forming cells | Increase % |
|---|---|---|
| Erythrocytes + saline solution | 3600 |  |
| Erythrocytes + FCA | 3300 |  |
| Erythrocytes + saline solution + "Substance A" 1mg/kg | 11500 | 330 |
| Erythrocytes + FIA + "Substance A" 1mg/kg | 15500 | 460 |
| Erythrocytes + saline solution + "Substance B" 1mg/kg | 22800 | 630 |

3. Accelerated formation of antibodies against influenza virus following administration of "Substance A" to mice 10 g Swiss mice were injected subcutaneously with UV inactivated PR 8 influenza virus in water, FIA or FIA containing various doses of "Substance A;" Groups of 5 mice were bled from the retro-orbital virus at weekly intervals starting 14 days later. Hemo-agglutination inhibiting titration were carried out on the pooled sera (HIRST G.K., Science (1941) 94, p. 22) and the geometric mean of four titration was calculated as is evidenced in Table III. Substance A stimulated antibody response at doses of 50 and 5 µg per mouse. At 42 days there was a twelvefold increase in antibody levels in the 50 µg group.

Table III

| Adjuvant | Antibody titrations | | | | |
|---|---|---|---|---|---|
|  | 14 | 21 | 28 | 35 | 42 |
| controls: saline solution + virus | 4.0 | 8.0 | 13.4 | 16.0 | 16.0 |
| Controls FIA + virus | 11.3 | 19.0 | 32.0 | 45.0 | 64.0 |
| FIA + virus + "Substance A" 50µg/mouse | 32.0 | 64.0 | 215.0 | 305.0 | 722.0 |
| FIA + virus + "Substance A" 5µg/mouse | 11.3 | 32.0 | 90.0 | 108 | 152 |
| FIA + virus + "Substance A" 0.5µg/mouse | 4.0 | 8.0 | 22.0 | 45.0 | 108.0 |

4. Increased formation of antibodies against virus Columbia SK

The properties of "Substance A" are also shown for other viruses such as Columbia SK. A vaccine was prepared and killed by exposing a preparation of high titration Columbia SK virus to U.V. light. In this test, the titration expressed as infecting power, was lowered from 8.32 to 1.85 log ufp/ml. This inoculum was injected to mice either alone or together with FIA including or not including "Substance A". As shown in Table IV, "Substance A" administered with the vaccine strongly stimulated the immunitary response 14 days later.

Table IV

| Treatment | Antibody titration after 14 days |
|---|---|
| Vaccine alone | 2 |
| Vaccine + FIA | 37 |
| Vaccine + FIA + "Substance A" 100 µg/mouse | 181 |

5. Protective action of "Substance A" on survival of mice infected with virus Columbia SK In this experiment, the virus was given in concentrations which caused the death of most of the treated animals. "Substance A", with FIA and a homologuous viral vaccine administered three weeks before the inoculation of virus protected from death a substantial proportion of animals and appreciably lengthened the time of their survival. "Substance A" appeared to be more efficient than Freund's complete adjuvant.

Table V

| Adjuvant | Mortality | | Mean time of survival (days) |
|---|---|---|---|
|  | Number of animals dead | Number of animals treated |  |
| Nil | 26 | 29 | 5.59 |
| FIA | 26 | 28 | 6.25 |
| FCA | 22 | 26 | 6.15 |
| FIA + "Substance A" 100µg/mouse | 20 | 29 | 7.28 |

B. Demonstration of inocuity of "Substance A"

The following tests demonstrate the lack of toxicity of "Substance A".

(1) Hyperreactivity to endotoxins

It is well established that mycobacteria increase the susceptibility to the lethal effect of endotoxins (Suter, E. and Coll. 1958, Proc. Soc. Exp. Biol. Med. 1958, 99, 167; Halpern, B. N. and Coll., C.R. Soc. Biol. Paris, 1958, 152 899).

It has been admitted that this activity is related to the "cord factor" (E. Suter et Coll., Proc. Soc. Exp. Biol. Med. 1958, 99, 1967).

Mice were sensitized 14 days before their being challenged with endotoxin, by injections, either with BCG (Bacille Calmette Guerin) killed by phenol and in the form of whole cells or delipidated cells, or by whole cells of *Mycobacterium smegmatis* killed by phenol. Two different samples either crude "Substance A" (not fractioned by "SEPHADEX") or of purified "Substance A" have also been tested. In each case, mice received intravenous injections at doses of 300 μg of the product under assay in suspension in saline or in "Bayol."

It should be noted that "Bayol" must be used at a final concentration of 50% to provide an adjuvant action, as in the case of complete Freund's adjuvant. However, in the experiments under consideration relating to the hyperreactivity towards an endotoxin (Table VI), the injections comprised in all cases 0.2 ml of mycobacterial preparations suspended in a medium containing 10% of "Bayol".

Two weeks later, all mice received an intravenous injection of an endotoxin preparation extracted from *Salmonella enteriditis*, strain Danysz. The $LD_{50}$ of this preparation suspended in saline and injected to normal controls corresponds to 240 μg.

As may be seen from Table VI:

a. $LD_{50}$ of endotoxin was multiplied by 200 when whole BCG has been administered to mice, while administration of delipidated BCG was without effect when the cells were suspended in a saline solute. However, when delipidated BCG was suspended in "Bayol", the sensitizing effect of this mycobacterial preparation was recovered. Injection of "Bayol" alone to controls did not sensitize mice to endotoxin.

b. Administration of whole heat-killed *M. smegmatis* (strain from which "Substance A" has been prepared) sensitized to a much smaller degree than BCG to endotoxins. Nevertheless the suspension of *M. smegmatis* in "Bayol" sensitized strongly the mice to endotoxin.

c. Crude "Substance A" did not sensitize to endotoxin when suspended in saline or even in "Bayol".

Table VI shows the amounts of endotoxin injected per mouse.

Table VI

| | Hyperreactivity to an endotoxin | | | | | | |
|---|---|---|---|---|---|---|---|
| | Endotoxin (μg per mouse) | | | | | | |
| | 0.15 | 0.5 | 1.5 | 5 | 15 | 50 | DL50 |
| Controls (Bayol) | — | — | 0/8+ | 0/8 | 0/15 | 0/15 | >50 |
| BCG* (saline solute) | 0/18 | 22/42 | 34/58 | 48/58 | 46/56 | 45/45 | 1.3 |
| BCG delipidated* (saline solute) | — | — | 0/8 | 0/8 | 1/33 | 4/33 | >50 |
| BCG delipidated* (Bayol) | — | — | 6/7 | 7/7 | 7/7 | 7/7 | <1.5 |
| *M. smegmatis** (saline solute) | — | — | 2/25 | 3/24 | 4/26 | 11/25 | 37.9 |
| *M. smegmatis** (Bayol) | — | 8/16 | 11/16 | 13/16 | 12/16 | 8/8 | 1.1 |
| "Substance A" crude* (saline solute) | — | — | 0/8 | 0/18 | 0/18 | 1/35 | >50 |
| "Substance A" crude* (Bayol) | — | — | 1/6 | 0/13 | 0/14 | 0/14 | >50 |
| "Substance A"* (Bayol) | — | — | — | — | — | 1/10 | >50 |

+Dead / total
*In each case, the dosage is 300 μg per mouse.

2. Lung granuloma and lymphoid hyperplasia

It is well established that upon being injected intravenously, mycobacteria cause hypertrophy of the liver and of the spleen as well as lung granuloma measurable by an increase of the weight of said organs, 3 to 14 days after injection. This latter activity can also be caused by "cord factor" suspended in paraffin oil (Bekierkunst et al., J. Bacteriol, 1969, 100, 95–102). In the following tests, mice received either cells (killed with phenol) of BCG or *M. smegmatis*, or "Substance A". BCG was suspended in saline, whereas *M. smegmatis* and "Substance A" were suspended either in saline, or in "Bayol" at a concentration of 10%. All injections were intravenous at a volume of 0.2 ml and the animals were sacrificed 14 days later.

As shown in Table VII, 300 μg of BCG suspended in saline caused substantial hepatomegaly and splenomegaly. Suspended in saline, 300 μg of *M. smegmatis* led to an increase of the weight of the lung and the spleen. These effects were considerably stronger when 300 μg of *M. smegmatis* were suspended in "Bayol" and, in this case, the liver was also hypertrophied. On the contrary, after injection of "Substance A" suspended in a saline solution or even in "Bayol", no detectable augmentation of the weight of various organs, compared to the controls, was noted.

3. Sensitivity to tuberculin

Guinea pigs were sensitized by subcutaneous injections of whole cells killed with phenol of BCG (0.2 or 2 mg), of *M. smegmatis* (2 mg) or *M. kansasii* (2 mg). A few guinea pigs were treated either with crude "Substance A" (0.2 or 2 mg) or with two different preparations of purified "Substance A" (0.2 mg). In all cases, mycobacterial substances were suspended in incomplete Freund's adjuvant (final concentration of "Bayol"=50%).

Table VII

| Absence of hypertrophy of lungs, liver or spleen after administration of "Substance A" | | | | | | | | |
|---|---|---|---|---|---|---|---|---|
| | | Number of mice | Weight of liver (mg) | | | Weight of spleen (mg) | | Weight of lungs (mg) |
| Controls | | 8 | 1073 | ± | 186 | 123 ± 38.8 | 153 ± 13.7 | |
| BCG 100 μg | | 7 | 1275 | ± | 311 | 170 ± 71.3 | 170 ± 14.9 | |
| BCG 300 μg | | 7 | 1767** | ± | 269 | 338** ± 107.3 | 170 ± 22.5 | |
| *M. smegmatis* 100 μg | saline solute | 7 | 1119 | ± | 160 | 139 ± 28 | 163 ± 19.2 | |
| *M. smegmatis* 300 μg | | 6 | 1215 | ± | 282 | 194* ± 63.7 | 182* ± 25.8 | |
| "Substance A" 100 μg | | 7 | 1115 | ± | 162 | 153 ± 35.5 | 158 ± 9.9 | |

Table VII-continued

| Absence of hypertrophy of lungs, liver or spleen after administration of "Substance A" | | | | | | | | | | | |
|---|---|---|---|---|---|---|---|---|---|---|---|
| | | Number of mice | Weight of liver (mg) | | | Weight of spleen (mg) | | | Weight of lungs (mg) | | |
| "Substance A" 300 μg | | 8 | 1065 | ± | 117 | 138 | ± | 35.8 | 161 | ± | 14.5 |
| Controls | | 7 | 1029 | ± | 159 | 118 | ± | 18.3 | 160 | ± | 23.6 |
| M. smegmatis 100 μg | | 8 | 1092 | ± | 202 | 156 | ± | 51.8 | 196 | ± | 38.1 |
| M. smegmatis 300 μg | "Bayol" | 8 | 1761** | ± | 382 | 321** | ± | 89.3 | 225** | ± | 31 |
| "Substance A" 100 μg | | 10 | 1050 | ± | 269 | 142 | ± | 64.6 | 171 | ± | 40.2 |
| "Substance A" 300 μg | | 9 | 1128 | ± | 238 | 157 | ± | 52.5 | 156 | ± | 21.8 |

Mice used in this test are hybrids $F_1$ (CBA/T6/T6 × AKR). Dosages are expressed in micrograms per mouse.
*P 0.05
**P 0.01

Table VIII

| Lack of sensitivity to tuberculin of "Substance A" | | | | | | |
|---|---|---|---|---|---|---|
| | Reaction at 100 i.u. of tuberculin | | | Reaction at 300 i.u. of tuberculin | | |
| | Diameter | Mean Diam. | intensity | Diameter | Mean Diam. | intensity |
| FIA + BCG 0,2 mg | 2-2-3-1-3-3 | 2.3 | + | 2-2-5-4-4-4 | 3.5 | ++ |
| FIA + BCG 2 mg | 8-6-7-4-6-3-4-3-5-6-5 | 5.2 | +++ | 10-8-12-9-10-8 | 9.5 | ++++ |
| FIA + M. smegmatis 2 mg | | | | 7 | 7 | +++ |
| FIA + M. kansasii 2 mg | 0-2-2-3-1-3-2-2-2-7-6-6 | 3 | ++ | 8-7-8-9-6 | 7.6 | +++ |
| FIA + "Substance A" crude 0.2 mg | 0-0-1 | 0.3 | — | 0-1-2 | 1 | + |
| FIA + "Substance A" crude 2 mg | 0-0-2-0 | 0.25 | — | 2-0 | 1 | + |
| + "Substance A" 0.2 mg | 0-0-0-0-0-0-0-0-0-0 | 0 | | 0-0-0-0-0-0-0-0-0-0 | 0 | — |

The sensitivity of these animals was measured 21 days later by intradermic injection of 100 I.U. or 300 I.U. tuberculin. Glycerol was also injected, as a control substance.

As seen in Table VIII, necrosis and strong cutaneous reactions were caused by tuberculin when guinea pigs had been sensitized by FIA containing BCG or M. smegmatis or M. kansassi, but these phenomena did not take place when the animals had been sensitized with "Substance A" added to Freund's incomplete adjuvant.

4. Pyrogenic activity

It is well known that numerous bacteria contain fever causing substances. The usual method for estimating the pyrogenic activity consists in injecting substances to rabbits and measuring the resulting rise of temperature.

Under these conditions, 0.01 μg/kg caused a fever response and with 0.05 μg/kg a substantial rise of temperature. BCG (whole cells) killed by phenol and "Substance A" were injected to rabbits at dosages of 5 to 100 μg/kg and the rise of temperature was determined at different times after administration. It is noted that 100 μg of BCG induced the same response than 0.05 μg of endotoxin and 100 μg of "Substance A" induced a rise in temperature which was only of the same order of magnitude was that obtained with 5 μg/kg of BCG.

These results are summarized in Table IX.

Table IX

| Preparation | Surface of area under temperature curve (cm²) | Maximum rise of temperature (°C) |
|---|---|---|
| Endotoxine (Difco LPS) 0.05 μg | 17.6 ± 1.9 | 1.33 ± 0.11 |
| BCG 5μg | 6.3 ± 1.7 | 0.78 ± 0.22 |
| BCG 100 μg | 17.0 ± 4.1 | 1.33 ± 0.28 |
| "Substance A" 5 μg | 2.8 ± 0.6 | 0.39 ± 0.11 |
| "Substance A" 100 μg | 9.6 ± 5.1 | 0.78 ± 0.39 |

5. Experimental polyarthritis of the rat

A mixture of paraffin oil and killed mycobacteria was used to induce experimental polyarthritis of the rat (Pearson and Wood, Arthr. and Rheum., 1959; 2: 440–459). This phenomenon is considered as an autoimmune reaction. Thus when complete Freund's adjuvant is injected in the foot pad of rats, there may be seen an articular oedema which is the most pronounced in the leg having received an injection with Freund's adjuvant but which is also visible in all the other articulations. Modifications at the articular level which may be measured by the volume or the weight of the legs are very substantial after 7 days and reach their maximum value 14 days after injection. The arthritis induced in this way is accompanied by variations of albumin/globulin ratios in the blood.

In the following test (Table X), groups of 10 rats received FIA containing either cells of M. tuberculosis (5 or 2 mg/ml) or "Substance A" (2 mg/ml). Further, two groups of controls received either an injection of saline solute alone or an injection of this solute containing "Substance A" (2 mg/ml). All injections were effected in one of the hind legs at a volume of 0.1 ml. The rats were killed 17 days later.

It is noted that the mixture of FIA and mycobacteria (even at a dosage of 2 mg/ml) increased considerably the volume of both hind legs, reduced the gain of the body weight and reversed the ratio of albumin to globulin. On the contrary, animals treated with "Substance A" in saline behaved like normal controls and, even when "Substance A" had been administered together with FIA, the albumin/globulin ratio and the body weight were not affected whereas the volume of both hind legs increased only slightly (Table X). This slight increase was moreover due to the presence of FIA alone, as will be shown by the following experiment.

In this experiment (Table XI), groups of ten rats received FIA in admixture either with mycobacteria (5 mg/ml) or with "Substance A" (5 mg/ml and 0.5 mg/ml). Moreover, two groups of control animals received an injection only of saline or of FIA. The injections were carried out under the same conditions as previously, but rats were killed 14 days later and arthritis was estimated by an increase of the weight of legs in relation to that of control animals.

It is noted that "Substance A", even at a dosage of 5 mg/ml, induced only a slight inflammation of the same order as that observed in the control animals having received only FIA and much smaller than in animals having received FIA and 5 mg of mycobacteria. Likewise, "Substance A" did not decrease the gain of body weight as in the case with a mixture of mycobacteria and FIA (Table XI).

Table X

|  | Hind legs | | Increase of body weight (%) | Albumin/globulin ratio |
|---|---|---|---|---|
|  | volume (ml) | increase (%) | | |
| Saline solute (controls) | 4.85 ± 0.064 | — | 100 | 2.18 ± 0.165 |
| FIA + Mycobacteria 5 mg/ml | 8.31 ± 0.471 | 100 | 42 | 0.70 ± 0.094 |
| FIA + Mycobacteria 2 mg/ml | 7.34 ± 0.315 | 72 | 71 | 0.68 ± 0.091 |
| Saline solute + "Substance A" 2 mg/ml | 4.71 ± 0.094 | 0 | 105 | 1.97 ± 0.165 |
| FIA + "Substance A" 2 mg/ml | 5.50 ± 0.136 | 19 | 104 | 1.73 ± 0.071 |

Table XI

|  | Hind legs | | Injected leg | | Increase of body weight (%) |
|---|---|---|---|---|---|
|  | Weight (g) | increase (%) | Weight (g) | Increase (%) | |
| Saline solute (controls) | 3.47 ± 0.121 | — | 1.74 ± 0.073 | — | 100 |
| FIA (controls) | 4.04 ± 0.235 | 27.08 | 2.31 ± 0.141 | 24.7 | 84.5 |
| FIA + Mycobacteria 5 mg/ml | 5.62 ± 0.146 | 100 | 4.05 ± 0.143 | 100 | 32.5 |
| FIA + "Substance A" 5 mg/ml | 4.10 ± 0.170 | 30.7 | 2.34 ± 0.123 | 26 | 89 |
| FIA + "Substance A" 0.5 mg/ml | 4.02 ± 0.242 | 27.1 | 2.31 ± 0.126 | 24.7 | 95 |

Comparison between adjuvant activity of preparations extracted from three different mycobacterial strains All the foregoing biological results were obtained with "Substance A" extracted from *M. smegmatis*. This water soluble fraction has also been prepared from *M. kansasii* or from BCG (see examples of preparations 2 and 3). The thus obtained preparations had also an adjuvant acivity. This activity has been established by measuring the serum antibodies in a guinea pig immunized by ovalbumin; in the following test (Table XII), this antigen was mixed with crude "Substance A" (before fractioning on "SEPHADEX") extracted from BCG or *M. kansasii*, the mixture being suspended in Freund's incomplete adjuvant. As previously, ovalbumin was administered to control animals either with FIA or with FCA. The conditions of the test are the same as in Example 1 (described in connection with Table I).

Numerical values in Table XII represent the mean value calculated on groups of six guinea pigs. Results are expressed as micrograms of antigen-antibody complex per ml of serum in the case of quantitative precipitation and as a reciprocal of serum titration in the case of hemo-agglutination.

It can be seen that "Substance A", whether extracted from *M. smegmatis*, BCG, or *M. kansasii*, stimulated the production of antibodies in the same way as Freund's complete adjuvant.

Table XII

|  | Quantitative precipitation | Hemo-agglutination (reciprocal of serum titration) |
|---|---|---|
| FCA | 2060 | 4640 |
| FIA (controls) | 100 | 440 |
| FIA + crude "Substance A" BCG* | 3940 | 5600 |
| FIA + crude "Substance A" *M. kansasii** | 3950 | 4640 |

*200 μg per guinea pig

D. Adjuvant activity of substances collected in the fractions corresponding to the "second peak" of elution of agents extracted from *M. smegmatis*

The product ("Substance B") made by lyophilisation of fractions corresponding to the "second peak" of elution of Example 1 possesses likewise, as already said, an adjuvant action. This action has been evidenced by measuring serum antibodies produced by ovalbumin administered in admixture with "Substance B" suspended in FIA. The effects of "Substance B" were compared to those of controls having received FIA or FCA.

Table XIII

| Products injected and | Quantitative precipitation |
|---|---|
| Controls FIA | 650 |
| Controls FCA | 4030 |
| FIA + "Substance B" 200 μg | 8200 |
| Controls FIA | 750 |
| Controls FCA | 3530 |
| FIA + "Substance B" repurified by a further filtration on SEPHADEX G50 50 μg | 4990 |

According to the invention, there are thus provided adjuvants having a considerable activity while free of objectionable side effects which have limited up to now the use of mycobacteria for preventing or treating diseases in animals and in men. Materials included within the scope of the present invention are used to increase the efficiency of vaccine whether of bacterial or viral origin, especially if they are weak immunogens. They can be used, in particular, to enhance immunization of the hosts (humans or animals) with respect to bacterial or viral diseases, antigens for tumors, protozoan antigens, etc. They may also be used efficiently for the production of serums. "Substance A" can be suspended in the incomplete Freund's adjuvant or in a carrier comprising, for instance, 8.5 parts hexadecane, 1.5 parts of Arlacel or glycerol monooleate and 10 parts of saline solution. The same is true for "Substance B".

Finally, it is particularly worth to note that "Substance A", under suitable conditions of use, may reveal its adjuvant activity even upon being added to antigen in an aqueous solution. The same is true for "Substance B".

The administration can be carried out in the form of typical compositions of the vaccine type, by intramuscular injection, intradermic injection, or subcutaneous injection, as well as scarification.

It is to be understood that the foregoing description has been given merely by way of an example, without any intent to limitation, the scope of the invention being defined by the appended claims.

What is claimed is:

1. A composition for stimulating immunization of a warm-blooded animal which comprises an antigen and an adjuvant, said adjuvant being a
   (1) water-soluble Mycobacteria or Nocardia-extracted polymer of a monomer, which monomer is a mucopeptide, free of its proteins and nucleic acids, linked with a glycolipid having an arabinogalactan,
   (2) the polymer having less than about 5% lipid content and the usual cell wall aminosugars and aminoacids;
   (3) the adjuvant being stable, insoluble in ether, chloroform, acetone and mixtures of ethanol-chloroform, and
   (4) the adjuvant being virtually free of hypersensitivity effects to tuberculin, having reduced pyrogenic effect and being virtually free of toxicity.

2. The composition of claim 1 wherein the adjuvant does not sensitize mice to endotoxin.

3. The composition of claim 1 wherein the cell wall aminoacids and aminosugars and other components of said adjuvant are defined as follows:
   12 to 15% aminosugars, consisting essentially of D-glucosamine and D-muramic acid, in equimolar proportions;
   12 to 15% aminoacids consisting essentially of L- and D-alanine, D-glutamic acid and meso-$\chi$-$\epsilon$-diaminopimelic acid, in a ratio of 1.3:1:1;
   60 to 70% neutral sugars consisting essentially of D-arabinose and D-galactose, in an approximate ratio of 2:1; and less than 5% lipids,
with an elemental analysis of 42.84% C, 6.49% H, 3.96% N, 0.1% P and 0% S.

4. The composition of claim 2 which has adjuvant activity in water-in-oil emulsion.

5. An aqueous solution of the composition of claim 1.

6. The composition of claim 1 wherein the water-soluble polymer is extracted from Mycobacterium.

7. The composition of claim 6 wherein the mycobacteria is Nocardia.

8. The composition of claim 1 wherein the polymer is extracted from Mycobacterium smegmatis.

9. The composition of claim 1 wherein the polymer is extracted from Mycobacterium kansasii.

10. An adjuvant, useful in water-in-oil emulsion for stimulating immunological responses in warm-blood animal, which adjuvant is a
    (1) water-soluble Mycobacteria- or Nocardia-extracted polymer of a monomer, which monomer is a mucopeptide, free of its proteins and nucleic acids, linked with a glycolipid having an arabinogalactan;
    (2) the polymer having less than about 5% lipid content and the usual cell wall aminosugars and aminoacids;
    (3) the adjuvant being stable, insoluble in ether, chloroform, acetone and mixtures of ethanol-chloroform, and
    (4) the adjuvant being virtually free of hypersensitivity effects to tuberculin and to an endotoxin, having reduced pyrogenic effect and being virtually free of toxicity.

11. The lyophilizate of claim 10.

12. The pharmaceutical composition useful in immunology of a warm-blooded animal which comprises a pharmaceutically acceptable carrier and the adjuvant of claim 10.

13. A method for stimulating immunization of a warm-blooded animal which comprises administering in an immunological amount, the composition of claim 12 which comprises an antigen and an adjuvant, said adjuvant being a
    (1) water-soluble polymer Mycobacteria or Nocardia extracted of a monomer, which monomer is a mucopeptide, free of its proteins and nucleic acids, linked with a glycolipid having an arabinogalactan;
    (2) the polymer having less than about 5% lipid content and the usual cell wall aminosugars and aminoacids;
    (3) the adjuvant being stable, insoluble in ether, chloroform, acetone and mixtures of ethanol-chloroform, and
    (4) the adjuvant being virtually free of hypersensitivity effects to tuberculin and to an endotoxin, having reduced pyrogenic effect and being virtually free of toxicity.

14. The method of claim 13 wherein the administration is performed with a water-in-oil emulsion.

15. The adjuvant of claim 10, wherein the cell wall aminoacids and aminosugars and other components of said adjuvant are defined as follows:
    12 to 15% aminosugars, consisting essentially of D-glucosamine and D-muramic acid, in equimolar proportions;
    12 to 15% aminoacids consisting essentially of L- and D-alanine, D-glutamic acid and meso-$\chi$-$\epsilon$-diaminopimelic acid, in a ratio of 1.3:1:1;
    60 to 70% neutral sugars consisting essentially of D-arabinose and D-galactose, in an approximate ratio of 2:1; and less than 5% lipids,
with an elemental analysis of 42.84% C, 6.49% H, 3.96% N, 0.1% P and 0% S.

16. The adjuvant of claim 10, wherein the water-soluble polymer is mycobacteria-extracted.

17. The adjuvant of claim 10, wherein the water-soluble polymer is Nocardia-extracted.

18. The method of claim 14, wherein the cell wall aminoacids and aminosugars and other components of said adjuvant are defined as follows:
    12 to 15% aminosugars, consisting essentially of D-glucosamine and D-muramic acid, in equimolar proportions;
    12 to 15% aminoacids consisting essentially of L- and D-alanine, D-glutamic acid and meso-$\chi$-$\epsilon$-diaminopimelic acid, in a ratio of 1.3:1:1;

60 to 70% neutral sugars consisting essentially of D-arabinose and D-galactose, in an approximate ratio of 2:1; and less than 5% lipids, with an elemental analysis of 42.84% C., 6.49% H., 3.96% N., 0.1% P. and 0% S.

19. The method of claim 13, wherein the water-soluble polymer is mycobacteria-extracted.

20. The method of claim 13, wherein the mycobacteria water-soluble polymer is Nocardia-extracted.

21. The method of claim 19, wherein the mycobacteria water-soluble polymer is extracted from Mycobacterium smegmatis.

22. The method of claim 19, wherein the mycobacteria water-soluble polymer is Mycobacterium kansasii.